United States Patent
Nishimura et al.

(10) Patent No.: US 12,121,550 B2
(45) Date of Patent: Oct. 22, 2024

(54) LACTIC ACID BACTERIUM, BLOOD IRON INCREASING AGENT, AND ANEMIA IMPROVING AGENT

(71) Applicant: ICHIBIKI CO., LTD., Nagoya (JP)

(72) Inventors: Atsuhisa Nishimura, Toyohashi (JP); Noriyuki Asai, Toyohashi (JP); Toshihiko Kumazawa, Toyohashi (JP)

(73) Assignee: ICHIBIKI CO., LTD., Nagoya (JP)

( * ) Notice: Subject to any disclaimer, the term of this patent is extended or adjusted under 35 U.S.C. 154(b) by 424 days.

(21) Appl. No.: 17/267,050

(22) PCT Filed: Aug. 16, 2019

(86) PCT No.: PCT/JP2019/032181
§ 371 (c)(1),
(2) Date: Feb. 9, 2021

(87) PCT Pub. No.: WO2020/036229
PCT Pub. Date: Feb. 20, 2020

(65) Prior Publication Data
US 2021/0228651 A1 Jul. 29, 2021

(30) Foreign Application Priority Data

Aug. 17, 2018 (JP) ................. 2018-153344
Jan. 21, 2019 (JP) ................. 2019-007716
Apr. 5, 2019 (JP) ................. 2019-072472

(51) Int. Cl.
| | |
|---|---|
| *A61K 35/74* | (2015.01) |
| *A61P 7/06* | (2006.01) |
| *C12N 1/20* | (2006.01) |
| *C12R 1/46* | (2006.01) |

(52) U.S. Cl.
CPC .......... *A61K 35/74* (2013.01); *A61P 7/06* (2018.01); *C12N 1/20* (2013.01); *C12R 2001/46* (2021.05)

(58) Field of Classification Search
CPC .......... A61K 35/74; A61K 2035/115; A61K 35/744; A61P 7/06; A61P 7/00; C12N 1/20; C12N 1/205; C12R 2001/46; C12R 2001/01
See application file for complete search history.

(56) References Cited

U.S. PATENT DOCUMENTS

| | | | |
|---|---|---|---|
| 11,260,085 B2 * | 3/2022 | Kumazawa | ............. C07K 14/57 |
| 2009/0098190 A1 | 4/2009 | Alenfall et al. | |
| 2011/0236360 A1 | 9/2011 | Ochi et al. | |

FOREIGN PATENT DOCUMENTS

| | | | | |
|---|---|---|---|---|
| CA | 3037601 A1 * | 3/2018 | ............. | A23K 10/18 |
| CN | 105969687 A | 9/2016 | | |
| EP | 3479837 A1 | 5/2019 | | |
| JP | H05-025051 A | 2/1993 | | |
| JP | H07-053391 A | 2/1995 | | |
| JP | 2008-544753 A | 12/2008 | | |
| JP | 2013-208071 A | 10/2013 | | |
| WO | 2006/080522 A1 | 8/2006 | | |
| WO | 2010/038714 A1 | 4/2010 | | |
| WO | 2011/114916 A1 | 9/2011 | | |
| WO | 2018/003899 A1 | 1/2018 | | |
| WO | 2019/009328 A1 | 1/2019 | | |

OTHER PUBLICATIONS

NCIMB, Tetragenococcus halophilus accession 9477; https://store.ncimb.com/page/Strains_table1; accessed Mar. 31, 2023 (Year: 1962).*
Conrad, Marcel E., and Jay N. Umbreit. "Iron absorption and transport—an update." American journal of hematology 64.4 (2000): 287-298. (Year: 2000).*
Ohata, Eriko, et al. "Tetragenococcus halophilus MN45 isolated from miso inhibits IgE production." Food Science and Technology Research 17.2 (2011): 129-138. (Year: 2011).*
Adiki, Shanta Kumari, et al. "Enhancement in iron absorption on intake of chemometrically optimized ratio of probiotic strain Lactobacillus plantarum 299v with iron supplement pearl millet." Biological trace element research 190.1 (2019): 150-156. (Year: 2019).*
Le, Bao, and Seung Hwan Yang. "Efficacy of Lactobacillus plantarum in prevention of inflammatory bowel disease." Toxicology reports 5 (2018): 314-317. (Year: 2019).*
Kaźmierczak-Siedlecka K, Daca A, Folwarski M, Witkowski J, Bryl E, Makarewicz W. The role of Lactobacillus plantarum 299v in supporting treatment of selected diseases. Central European Journal of Immunology. 2020;45(4):488-493. doi: 10.5114/ceji.2020.101515. (Year: 2020).*
Rivera, A. J., et al. "Microbial communities and gene contributions in smokeless tobacco products." Applied microbiology and biotechnology 104 (2020): 10613-10629. (Year: 2020).*
LTK-1N; https://www.ichibiki.co.jp/prouse/lactic-acid-bacterium/60912_2/; accessed Mar. 31, 2023 (Year: 2023).*
Macfarlane, Bruce J., et al. "Effect of traditional oriental soy products on iron absorption." The American journal of clinical nutrition 51.5 (1990): 873-880. (Year: 1990).*
Tamang, Buddhiman, and Jyoti P. Tamang. "Lactic acid bacteria isolated from indigenous fermented bamboo products of Arunachal Pradesh in India and their functionality." Food Biotechnology 23.2 (2009): 133-147. (Year: 2009).*
Natanzi, Mahboobeh Mehrabani, Sayyed Mohammad Hossein Ghaderian, and Zohreh Khodaii. "Iron absorption improvement: an additional health benefit for certain probiotics, in vitro and in vivo study." Acta Medica Mediterranea 33.2 (2017): 295-300. (Year: 2017).*
Fabiano, Angela, et al. "Sucrosomial® iron absorption studied by in vitro and ex-vivo models." European Journal of Pharmaceutical Sciences 111 (2018): 425-431. (Year: 2018).*
International Search Report mailed Nov. 12, 2019, issued for PCT/JP2019/032181.

(Continued)

*Primary Examiner* — Louise W Humphrey
*Assistant Examiner* — Candice Lee Swift
(74) *Attorney, Agent, or Firm* — Locke Lord LLP

(57) ABSTRACT

A lactic acid bacterium is provided which has high foodstuff suitability, easy to manufacture, and can increase the blood iron concentration, thereby improving anemia. A lactic acid bacterium of salt-tolerant that increases the blood iron concentration.

10 Claims, No Drawings

(56) References Cited

OTHER PUBLICATIONS

G. Zhao et al., "Functional properties of soy sauce and metabolism genes of strains for fermentation", International Journal of Food Science and Technology, vol. 48, No. 5, May 1, 2013, pp. 903-909. (cited in the May 4, 2022 Search Report issued for EPEP19849264.7).

S. Masuda et al., "Immunomodulatory effect of halophilic lactic acid bacterium *Tetragenococcus halophilus* Th221 from soy sauce moromi grown in high-salt medium", International Journal of Food Microbiology, Elsevier BV, NL, vol. 121, No. 3, Nov. 1, 2007, pp. 245-252. (cited in the May 4, 2022 Search Report issued for EPEP19849264.7).

H-W Lee et al., "Relationship between chemical characteristics and bacterial community of a Korean salted-fermented anchovy sauce, Myeolchi-Aekjeot", LWT—Food Science and Technology, Academic Press, United Kingdom, vol. 73, Jun. 4, 2016, pp. 251-258. (cited in the May 4, 2022 Search Report issued for EPEP19849264.7).

Supplementary European Search Report mailed May 4, 2022, issued for European Patent Application No. EP19849264.7.

\* cited by examiner

LACTIC ACID BACTERIUM, BLOOD IRON INCREASING AGENT, AND ANEMIA IMPROVING AGENT

TECHNICAL FIELD

The present invention relates to a lactic acid bacterium, a blood iron increasing agent, and an anemia improving agent. More particularly, the present invention relates to a lactic acid bacterium, a blood iron increasing agent, and an anemia improving agent which are highly suitable for foods, easy to manufacture, and can increase the blood iron concentration, thereby improving anemia.

BACKGROUND ART

According to the results of the National Health and Nutrition Survey in 2016, the average ingestion amount of most nutrients exceeded the estimated requirement, but the iron content (iron) of adult women (with menstruation) is still lacking.

As iron deficiency continues, storage iron, such as mainly ferritin, decrease, followed by decreased hemoglobin and serum iron, leading to iron deficiency anemia.

The state in which the storage iron is lowered is said to be a latent iron deficiency in which the anemia symptom does not appear (so-called "silent iron deficiency"), and although it is not a disease, it may be a cause of a physical disorder (indefinite complaint) such as "somehow feel fatigue", "work inefficiency", or "not motivated" in some cases. In addition, recent studies have also suggested that decreased storage iron may be associated with insomnia and depressive symptoms. Such a "silent iron deficiency" has become a serious problem in the modern times when the social participation of women is increasing.

As a cause of the iron deficiency, there is known a problem such as a deviation of the diet. In order to solve this iron deficiency, it is important to improve the diet and to have a proper diet. In order to improve the diet, it is important to actively ingest animal foods such as livestock meat and fish meat rich in iron (heme iron) with high absorption rate, and to ingest vegetables, beans and seaweeds rich in iron (non-heme iron) with low absorption rate together with vegetables rich in vitamins that enhance the absorption.

However, women who tend to be iron-deficient are generally more likely to eat vegetarian foods, so it is not easy to increase the ingestion of animal foods. There is also a problem that excessive ingestion of habitual animal foods is prone to obesity and increases the risk of developing lifestyle-related diseases such as arteriosclerosis and cerebral infarction.

Thus, it is not easy to improve the diet. Therefore, if symptoms of iron deficiency have progressed, it is effective to take iron preparations. However, the iron preparations should not be easily taken because the side effects of iron may include gastrointestinal symptoms such as abdominal pain, nausea, vomiting, diarrhea, and constipation. When taking the iron preparations, vitamin C may be used in combination to enhance the absorption effect of iron. but vitamin C is degraded by stomach acid, so there is a problem that the effect cannot be expected unless a large dose such as 1000 mg/dose is taken.

Surprisingly, sports players are also often suffering from anemia (so-called sports anemia), which is one of the most common medical illnesses among sports players.

The causes of sports anemia are (1) iron loss due to sweat during exercise (iron deficiency anemia), requiring a large amount of iron because of the high activity of sports players, and (2) anemia caused by physical destruction of red blood cells in blood (motility hemolytic anemia). It is known that this motility hemolytic anemia is particularly likely to occur in sports that the sole of the foot is heavily impacted (e.g., long distance sports such as marathon and athletic sports, volleyball, soccer, basketball, karate, kendo, etc.).

As a countermeasure against such sports anemia, prescription of iron preparation (taking tablets, injection of iron preparation, etc.) has been carried out.

Here, in general, most of the iron in the body is present in the red blood cells as hemoglobin, and plays a role of transporting oxygen to the whole body.

In the case of endurance exercise (exercise requiring endurance), glucose is used at the beginning of exercise to produce energy, followed by fat and glycogen in muscles. Oxygen is required for such energy production (a state doing so-called aerobic exercise). At this time, if hemoglobin (iron in the blood) is high, oxygen can be efficiently transported to the whole body, which can be expected to lead to an increase in endurance. For this reason, there were actual situations in which instructors who instructed athletes in junior and senior high school age had athletes (players) use iron for the purpose of improving their competitive abilities, and athletes such as business teams themselves used them for the purpose of improving their competitive abilities.

However, there is concern that excessive iron ingestion may cause functional impairment of the liver, etc., and the Japan Association of Athletics Federations provided guidelines for prohibiting "injection of iron preparation" which has been used for anemia countermeasures in principle.

Against this background, it has been desired to develop blood iron increasing agents and anemia improving agents which increase the utilization efficiency of iron and eliminate side effects. The "blood iron increasing agent" herein means a substance having an effect of increasing iron in blood (including heme iron typified by hemoglobin, storage iron such as ferritin and hemosiderin, and serum iron).

Here, it is known to use lactic acid bacterium as a component of a blood iron increasing agent and an anemia improving agent having no side effect, and for example, a composition for treating iron deficiency anemia containing fermented milk obtained by using lactic acid bacterium belonging to *Lactobacillus acidophilus* has been reported (for example, see Patent Document 1). Since the lactic acid bacterium has conventionally been ingested through food, it has advantages of high safety to the human body and low concern about side effects.

The lactic acid bacterium has long been used for the production of fermented foods, and are ingested through these fermented foods. In addition, the lactic acid bacterium is known to have a variety of effects, specifically, intestinal regulation, intestinal bacterial flora improvement, cholesterol reduction, anti-obesity, cognitive function improvement, and cosmetic effects, etc. are reported. The lactic acid bacterium is also known to have immune improvement (allergy improvement, cancer prevention, and infection protection) effects.

CITATION LIST

Patent Documents

[Patent Document 1] JP-A-H07-53391

SUMMARY OF THE INVENTION

Problem to be Solved by the Invention

However, in the composition for treating iron deficiency anemia described in Patent Document 1, since a step of preparing a fermented milk using the above lactic acid bacterium is required in its production, a facility and a time for fermentation are also required. Further, the lactic acid bacterium itself used for manufacturing the composition for treating iron deficiency anemia described in Patent Document 1 also has a problem in that it requires labor and cost in manufacturing, for example, it is necessary to sufficiently prepare an environment at the time of its growth, or it is necessary to process a culture solution strictly.

Therefore, there has been a demand for the development of lactic acid bacterium which can increase the blood iron concentration and can improve the anemia, and which can be easily cultured, a blood iron increasing agent and an anemia improving agent which have the above effect by using the lactic acid bacterium and are simple to manufacture.

The present invention provides a lactic acid bacterium capable of increasing the blood iron concentration and improving anemia, a blood iron increasing agent containing the lactic acid bacterium, and an anemia improving agent containing the lactic acid bacterium.

Means for Solving the Problems

According to the present invention, the following lactic acid bacterium, blood iron increasing agent, and anemia improving agent are provided.
 [1] A lactic acid bacterium of salt-tolerant that increases the blood iron concentration.
 [2] The lactic acid bacterium according to [1], which is isolated in a brewing process of miso.
 [3] The lactic acid bacterium according to [1] or [2], wherein a proliferation rate is 30 times or more when cultured in a medium having a salinity of 12 w/v %.
 [4] The lactic acid bacterium according to any one of the above [1] to [3], which is *Tetragenococcus halophilus*.
 [5] The lactic acid bacterium according to any one of [1] to [4], which is a lactic acid bacterium of Accession number NITE BP-02318 or a lactic acid bacterium of Accession number NITE BP-03010.
 [6] A blood iron increasing agent containing the lactic acid bacterium according to any one of [1] to [5] above.
 [7] An anemia improving agent containing the lactic acid bacterium according to any one of [1] to [5] above.

Effect of the Invention

The lactic acid bacterium of the present invention is easy to manufacture because of its high foodstuff suitability (that is, highly safe) and simple culture. Furthermore, the lactic acid bacterium of the present invention is capable of increasing the blood iron concentration and improving anemia.

Since the blood iron increasing agent of the present invention contains the lactic acid bacterium of the present invention, it has high foodstuff suitability (that is, highly safe) and easy to manufacture, and further, it is capable of increasing the blood iron concentration and improving anemia.

Since the anemia improving agent of the present invention contains the lactic acid bacterium of the present invention, it has high foodstuff suitability (that is, highly safe) and is easy to manufacture, and further, it is capable of increasing the blood iron concentration and improving anemia.

MODE FOR CARRYING OUT THE INVENTION

Hereinafter, embodiments for carrying out the present invention will be described, but the present invention is not limited to the following embodiments. That is, it is to be understood that, within a range not departing from the gist of the present invention, those to which the following embodiments are appropriately modified, improved, and the like are added are also included in the scope of the present invention based on the ordinary knowledge of a person skilled in the art.

[1] Lactic acid bacterium:

The lactic acid bacterium of the present invention is a lactic acid bacterium having salt tolerance, which increases the blood iron concentration. The lactic acid bacterium is easy to manufacture because of their high foodstuff suitability (i.e., highly safe) and simple culturing. Furthermore, the lactic acid bacterium of the present invention is capable of increasing the blood iron concentration and improving anemia. Note that the lactic acid bacterium in the present invention can be *Tetragenococcus halophilus*. "The blood iron concentration" means the concentration of serum iron, storage iron (e.g., ferritin, hemosiderin), and heme iron (e.g., hemoglobin).

Here, for example, the composition for treating iron deficiency anemia described in Patent Document 1 contains fermented milk, and a predetermined lactic acid bacterium is utilized in manufacturing this fermented milk. Therefore, it is not disclosed that the lactic acid bacterium itself is involved in the absorption of iron. On the other hand, the present invention is that a predetermined lactic acid bacterium exhibits the above-mentioned effect.

In addition, when an ordinary lactic acid bacterium (a lactic acid bacterium which does not have salt tolerance) is manufactured commercially, concentration and purification of a bacterial cell, treatment of a culture solution (e.g., sterilization by an autoclave equivalent), and the like are necessary. In addition, it is necessary to maintain an environment in which contaminants such as unwanted bacteria are not contaminated at the time of cultivation, which is laborious and costly to manufacture. On the other hand, since the lactic acid bacterium of the present invention has salt tolerance, it is possible to culture in an environment having a high salinity, which is an environment in which contaminants are difficult to proliferate, and it is easy to culture in a state in which proliferation of contaminate is suppressed.

In the present specification, "increasing the blood iron concentration" means that the blood iron concentration increases before and after ingestion by continuous oral ingestion of the lactic acid bacterium. It is preferable that "increasing the blood iron concentration" specifically means that the blood iron concentration is significantly increased, and more specifically, it is preferable that the blood iron concentration has the capability of increasing the iron concentration so that there is a significant difference in the risk rate (significance level) of 5% or less when the test is performed by Wilcoxon signed rank test.

In the present specification, "having salt tolerance" means that it has a property of being capable of culturing in a medium having a high salinity (specifically, a salinity of 11 w/v % or more). As the degree of salt tolerance, it is preferable that the proliferation rate is 30 times or more when cultured in a medium having a salinity of 12 w/v %.

The lactic acid bacterium of the present invention may be, for example, those isolated in a brewing process of miso (particularly, rice miso). Specific examples of the lactic acid bacterium having salt tolerance isolated in the brewing process of rice miso include a trade name "Lactic acid bacterium Kurahana LTK-1" (manufactured by Ichibiki Co., Ltd.).

The lactic acid bacterium "isolated in the brewing process of miso" refer to the lactic acid bacterium having salt tolerance fixed to "Kura (storage)," "Muro (chamber)," "Oke (tub)" and the like in the brewing process of miso. Furthermore, it refers to a bacterium which can grow from the preparation to the ripening process of miso. The lactic acid bacterium "isolated in the brewing process of miso" can also be referred to as salt-tolerant lactic acid bacterium (i.e., miso lactic acid bacterium) contained in miso, or in other words, salt-tolerant lactic acid bacterium derived from miso (i.e., salt-tolerant lactic acid bacterium originating from miso). In the present invention, lactic acid bacterium "isolated in the brewing process of miso" are not limited to lactic acid bacterium isolated in the brewing process of miso, but also include lactic acid bacterium isolated in the brewing process of miso and cultured (subcultured) thereafter.

As described above, the lactic acid bacterium of the present invention is not particularly limited as long as it is a lactic acid bacterium which increases the blood iron concentration and has salt tolerance, for example, a lactic acid bacterium of Accession Number NITE BP-02318, a lactic acid bacterium of Accession Number NITE BP-03010 (ICK-3 Strain), ICK-4 Strain, ICK-5 Strain, No. 185 Strain, No. 259 Strain, and No. 448 Strain, described in Example 4 to be described later can be included. Among them, the lactic acid bacterium of Accession Number NITE BP-02318, the lactic acid bacterium of Accession Number NITE BP-03010, ICK-4 Strain, and ICK-5 Strain, described in Example 4 to be described later are preferably used. Such a lactic acid bacterium having salt tolerance includes, specifically, *Tetragenococcus halophilus*.

The lactic acid bacterium of Accession Number NITE BP-02318 were deposited with the NITE Patent Microorganisms Depositary (NPMD), National Institute of Technology and Evaluation on Aug. 3, 2016 (date of domestic deposit), and they were transferred to the international depositary based on the Budapest Treaty on Sep. 6, 2017. The lactic acid bacterium of Accession Number NITE BP-03010 were internationally deposited with the NITE Patent Microorganisms Depositary (NPMD), National Institute of Technology and Evaluation on Aug. 5, 2019.

The lactic acid bacterium of the present invention may be a dead cell or a viable cell.

[2] The method for culturing lactic acid bacterium of the present invention:

Although there is no particular limitation on the culture condition of the lactic acid bacterium of the present invention, for example, it can be cultured in a medium having a salinity of 11 to 18 w/v %, and is preferably set to a salinity of 11 to 16 w/v %, and particularly preferably set to 12 to 14 w/v %. Note that "w/v %" means (mass (g)/volume (100 mL)) %.

When cultured under such conditions, other bacteria (contaminants such as unwanted bacteria) are difficult to grow, while the lactic acid bacterium of the present invention can be cultured so that the lactic acid bacterium of the present invention can be mainly cultured easily and favorably. Furthermore, culturing at salinity in the above range prevents proliferation of contaminants that do not have salt tolerance, while increasing the rate of proliferation over bacteria that have salt tolerance (salt-tolerant contaminants), such as salt-tolerant *Staphylococcus* bacteria. That is, even in relation to contaminants having salt tolerance, the culture can be terminated and recovered before the contaminant grows. When cultured in a medium having a salinity of less than 11 w/v %, contaminants grow easily, and it tends to be difficult to ensure a sufficient yield. In addition, when cultured in a medium having a salinity of more than 18 w/v %, the contaminants become more difficult to grow, but in order to obtain a necessary yield, the number of days of culturing becomes longer, so that the salt-tolerant contaminants will grow.

As described above, when cultured in a medium having the above salinity, it is possible to culture the lactic acid bacterium of the present invention efficiently and in a large amount even in a culture device of a simple open system (provided that it is capable of sterilization and heat insulation), without using a special device such as a sterile culture device of a closed system.

The culture temperature is preferably 20 to 40° C., more preferably 28 to 37° C. The culturing time is about 24 to 120 hours, and may be stirred during the culture. In addition, the pH of the medium is preferably 5 to 9, and more preferably 6 to 7.

The medium containing a nitrogen source and a carbon source can be used.

The nitrogen source is not particularly limited, and examples thereof include soy sauce, miso, meat extract, peptone, gluten, casein, yeast extract, and amino acids. Further, the carbon source is not particularly limited, and examples thereof include glucose, a koji digestive solution, a saccharification solution of rice, sucrose, starch, powdered corn syrup, and glycerin. In addition to the nitrogen source and the carbon source, for example, an inorganic salt such as sodium acetate, magnesium, manganese, or iron may be contained as an inorganic material, and vitamins and the like may be contained.

[3] Process for the preparation of lactic acid bacterium of the present invention The lactic acid bacterium of the present invention can be prepared by performing a treatment such as sterilization after culturing. Specifically, after culturing, a medium component containing salt is removed by means such as centrifugation, and the remaining lactic acid bacterium was washed and purified. Then, the lactic acid bacterium was heat sterilized, and then dried and concentrated by means such as freeze drying, vacuum drying, and hot air drying. In this way, the lactic acid bacterium of the present invention can be prepared.

Note that, although there is no particular limitation on the heat sterilization, specifically, autoclave sterilization (121° C., 20 minutes) or the same degree of sterilization is preferable.

[4] Ingestion period of lactic acid bacterium:

The lactic acid bacterium of the present invention preferably continues to be ingested for 2 weeks or more, and more preferably for 4 weeks or more.

[5] Blood iron increasing agents:

The blood iron increasing agent of the present invention contains the lactic acid bacterium of the present invention, and is capable of increasing the blood iron concentration by ingesting for a certain period of time. In addition, since the above-mentioned lactic acid bacterium is easily cultured because of its salt tolerance, the blood iron increasing agent of the present invention using the lactic acid bacterium is easily manufactured. The blood iron increasing agent of the present invention is also capable of increasing the blood iron concentration by containing the lactic acid bacterium of the present invention, and as a result, it exhibits an effect that anemia can be improved.

[5-1] Lactic acid bacterium:

The blood iron increasing agent of the present invention contains the lactic acid bacterium of the present invention described above as an active ingredient. By adopting the lactic acid bacterium, the blood iron concentration can be increased, and as a result, the anemia can be improved. Further, by adopting the lactic acid bacterium, it is highly safe and easy to manufacture. Note that, as the lactic acid bacterium, a kind of bacterial strain may be contained, or 2 or more kinds of bacterial strains may be contained.

As long as the blood iron increasing agent of the present invention contains the lactic acid bacterium of the present invention as an active ingredient, the content ratio thereof is not particularly limited and can be appropriately determined. For example, the lactic acid bacterium of the present invention may be contained so as to ingest from about 10 billion (equivalent to about 2.5 mg) to about 5 trillion (equivalent to about 1.25 g) in the number of bacteria per 1 time. The blood iron increasing agents may be taken orally before or after eating as medicines or supplements.

The blood iron increasing agent of the present invention may contain a culture, a bacterial cell or a bacterial component obtained by the method for culturing lactic acid bacterium of the present invention.

[5-2] Other ingredients:

The blood iron increasing agent of the present invention may be composed only of lactic acid bacterium of the present invention (or those containing a culture or the like), or may contain other ingredients other than the lactic acid bacterium of the present invention.

As the other ingredient, the ingredient which is appropriately blended according to the use of a medicine, a quasi-drug, a food and drink, or the like can be adopted.

In the case of medicines and quasi-drugs, examples of other ingredients include excipients, coating agents, binding agents, extender, disintegrants, surfactants, lubricants, diluents, dispersants, buffer, osmotic pressure regulators, pH regulators, emulsifier, antiseptic, stabilizer, antioxidants, colorants, ultraviolet absorbers, humectants, thickener, activity enhancing agents, anti-inflammatory agents, germicide, flavoring substances, flavoring agents, and the like. Combinations with iron salts are also effective. The iron salt may be any of an inorganic iron salt and an organic iron salt. It is to be noted that, as long as the object of the present invention is not impaired, an active ingredient or a pharmacological ingredient other than the lactic acid bacterium of the present invention may be contained.

In the case of food and drink, examples of other ingredients include sweeteners, acidulants, carbon dioxide gases, inorganic salts, perfumes, fruit juices, vitamins, antioxidants, esters, pigments, emulsifiers, preservatives, seasonings, vegetable extracts, flower nectar extracts, quality stabilizers, bitterness inhibitors, and the like. In addition, also in the case of food and drink, as long as the object of the present invention is not impaired, an active ingredient or a pharmacological ingredient other than the lactic acid bacterium of the present invention may be contained.

The blood iron increasing agent of the present invention can be ingested in any form (form of oral ingestion or form of parenteral ingestion). For example, in the case of oral ingestion, it is in solid forms such as tablets, coated tablets, granules, powders, and capsules, liquid forms such as elixirs and syrups, and the like.

[6] Method for manufacturing blood iron increasing agent:

The blood iron increasing agent of the present invention can be manufactured, for example, by a method comprising a lactic acid bacterium preparation step and a raw material preparation step. By such a manufacturing method, the blood iron increasing agent can be easily manufactured. In this method, as compared with the method for manufacturing a composition for treating iron deficiency anemia described in Patent Document 1, a step of obtaining fermented milk using a lactic acid bacterium is unnecessary, and a time, a facility, and the like for fermentation can be omitted, so that it can be referred to as a simple method. Further, as for the lactic acid bacterium itself, since it has salt tolerance, there is an advantage that it is easy to culture.

The lactic acid bacterium preparation step is a step of preparing the lactic acid bacterium of the present invention described above. The lactic acid bacterium may be prepared by obtaining a starter culture and culturing the starter by the above-described methods, or may be prepared by purchasing a commercially available lactic acid bacterium (for example, trade name "Lactic acid bacterium Kurahana LTK-1" (manufactured by Ichibiki Co., Ltd.).

The raw material preparation step is a step of preparing a raw material of a blood iron increasing agent by mixing the lactic acid bacterium of the present invention prepared in the lactic acid bacterium preparation step and, if necessary, other ingredients.

Note that, when the blood iron increasing agent of the present invention is composed only of the lactic acid bacterium of the present invention (or those containing the culture or the like), this step is not necessary. At this point, in the method for manufacturing a composition for treating iron deficiency anemia described in Patent Document 1, it is necessary to prepare a raw material by mixing fermented milk and an iron salt. On the other hand, when it is composed only of the lactic acid bacterium or the like of the present invention, since this step is not necessary, it becomes easy to manufacture even in this point.

In the case of a solid form such as a tablet, a step (state forming step) for forming a solid form may be employed after the raw material preparation step.

[7] Ingestion period of blood iron increasing agent:

The blood iron increasing agent of the present invention preferably continues ingestion for 2 weeks or more, and more preferably continues ingestion for 4 weeks or more.

[8] Anemia improving agent:

The anemia improving agent of the present invention contains the lactic acid bacterium of the present invention, and when ingested for a certain period of time, it increases the blood iron concentration, and as a result, it can improve anemia (particularly, iron deficiency anemia). Then, since the above-mentioned lactic acid bacterium are easily cultured because they are salt-tolerant, the anemia improving agent of the present invention using the lactic acid bacterium is easily manufactured. Then, the anemia improving agent of the present invention is also capable of increasing the blood iron concentration by containing the lactic acid bacterium of the present invention, and as a result, the effect of improving anemia is also exhibited.

The anemia improving agent of the present invention contains the lactic acid bacterium of the present invention, and may contain the blood iron increasing agent of the present invention. For example, the lactic acid bacterium of the present invention may be contained so as to ingest from about 10 billion (equivalent to about 2.5 mg) to about 5 trillion (equivalent to about 1.25 g) in the number of bacteria per 1 time. The anemia improving agent may be ingested orally before or after eating as a medicine or a supplement.

[8-1] Lactic acid bacterium:

The anemia improving agent of the present invention contains the lactic acid bacterium of the present invention described above as an active ingredient. By adopting the lactic acid bacterium, the blood iron concentration can be increased, and as a result, the anemia can be improved. Further, the anemia improving agent of the present invention is highly safe and easy to manufacture by adopting the above-mentioned lactic acid bacterium. Note that, as the lactic acid bacterium, a kind of bacterial strain may be contained, or 2 or more kinds of bacterial strains may be contained.

As long as the anemia improving agent of the present invention contains the lactic acid bacterium of the present invention as an active ingredient, the content ratio thereof is not particularly limited and can be appropriately determined.

The anemia improving agent of the present invention may contain a culture, a bacterial cell or a bacterial component obtained by the method for culturing a lactic acid bacterium of the present invention.

[8-2] Other ingredients:

The anemia improving agent of the present invention may be composed only of the lactic acid bacterium of the present invention (or those containing the culture or the like), or may contain other ingredients other than the lactic acid bacterium of the present invention.

As the other ingredient, the ingredient which is appropriately blended according to the use of a medicine, a quasi-drug, a food and drink, or the like can be adopted.

In the case of medicines and quasi-drugs, examples of other ingredients include excipients, coating agents, binding agents, extender, disintegrants, surfactants, lubricants, diluents, dispersants, buffer, osmotic pressure regulators, pH regulators, emulsifier, antiseptic, stabilizer, antioxidants, colorants, ultraviolet absorbers, humectants, thickener, activity enhancing agents, anti-inflammatory agents, germicide, flavoring substances, flavoring agents, and the like. Combinations with iron salts are also effective. The iron salt may be any of an inorganic iron salt and an organic iron salt. It is to be noted that, as long as the object of the present invention is not impaired, an active ingredient or a pharmacological ingredient other than the lactic acid bacterium of the present invention may be contained.

In the case of food and drink, examples of other components include sweeteners, acidulants, carbon dioxide gases, inorganic salts, perfumes, fruit juices, vitamins, antioxidants, esters, pigments, emulsifiers, preservatives, seasonings, vegetable extracts, flower nectar extracts, quality stabilizers, bitterness inhibitors, and the like. In addition, also in the case of food and drink, as long as the object of the present invention is not impaired, an active ingredient or a pharmacological ingredient other than the lactic acid bacterium of the present invention may be contained.

The anemia improving agent of the present invention can be ingested in any form (form of oral ingestion or form of parenteral ingestion). For example, in the case of oral ingestion, it is in solid forms such as tablets, coated tablets, granules, powders, and capsules, liquid forms such as elixirs and syrups, and the like.

Note that the anemia improving agent of the present invention may be prepared by mixing the blood iron increasing agent of the present invention described above with the other ingredients described above, or the blood iron increasing agent of the present invention may be used as it is (that is, it may be composed only of the blood iron increasing agent of the present invention).

[9] Method for manufacturing anemia improving agent:

The anemia improving agent of the present invention can be manufactured by the same method as that of the method for manufacturing the blood iron increasing agent of the present invention, and can be manufactured by, for example, a method comprising a lactic acid bacterium preparation step and a raw material preparation step. By such a manufacturing method, the anemia improving agent can be easily manufactured. In this method, as compared with the method for manufacturing a composition for treating iron deficiency anemia described in Patent Document 1, a step of obtaining fermented milk using a lactic acid bacterium is unnecessary, and a time, a facility, and the like for fermentation can be omitted, so that it can be referred to as a simple method. Further, as for the lactic acid bacterium itself, since it has salt tolerance, there is an advantage that it is easy to culture.

The lactic acid bacterium preparation step is a step of preparing the lactic acid bacterium of the present invention described above. The lactic acid bacterium may be prepared by obtaining a starter culture and culturing the starter by the above-described methods, or may be prepared by purchasing a commercially available lactic acid bacterium (for example, trade name "Lactic acid bacterium Kurahana LTK-1" (manufactured by Ichibiki Co., Ltd.).

The raw material preparation step is a step of preparing a raw material of an anemia improving agent by mixing a lactic acid bacterium of the present invention prepared in the lactic acid bacterium preparation step and, if necessary, other ingredients.

Note that, when the anemia improving agent of the present invention is composed only of the lactic acid bacterium of the present invention (or those containing the culture or the like), this step is not necessary. At this point, in the method for manufacturing a composition for treating iron deficiency anemia described in Patent Document 1, it is necessary to prepare a raw material by mixing fermented milk and an iron salt. On the other hand, when it is composed only of the lactic acid bacterium or the like of the present invention, since this step is not necessary, it becomes easy to manufacture even in this point.

In the case of a solid form such as a tablet, a step (state forming step) for forming a solid form may be employed after the raw material preparation step.

[10] Ingestion period of anemia improving agent:

The anemia improving agent of the present invention preferably continues ingestion for 2 weeks or more, and more preferably continues ingestion for 4 weeks or more.

EXAMPLES

Hereinafter, the present invention will be specifically described based on Examples, but the present invention is not limited to these Examples.

Example 1

The measurements of the iron concentration of serum (the serum iron concentration) were performed 20 healthy Japanese over 20 years old and under 45 years old before and after (on the 14th and 28th days) ingestion of the lactic acid bacterium. Note that the serum iron concentration was measured using a colorimetric method.

As a method for ingesting the lactic acid bacterium, tablets (blood iron increasing agent, anemia improving agent) containing the lactic acid bacterium of the present invention (specifically, the lactic acid bacterium of Accession Number NITE BP-02318) and the trade name "Lactic acid bacterium Kurahana LTK-1" (manufactured by Ichibiki Co., Ltd.) were ingested orally together with water (10 tablets per day (containing 1250 mg of "Lactic acid bacterium Kurahana LTK-1"). The ingestion period was 28 days. The results are shown in Table 1.

The safety of ingestion of the trade name "Lactic acid bacterium Kurahana LTK-1" was also confirmed, and adverse events related to the drug were not confirmed.

Ingredients of orally ingested tablets are as follows: The trade name "Lactic acid bacterium Kurahana LTK-1" was 41.7% by mass, dextrin was 39.0% by mass, powdered cellulose was 15.0% by mass, sucrose fatty acid ester was 2.0% by mass, fine particulate silicon dioxide was 2.0% by mass, and shellac was 0.3% by mass.

TABLE 1

|  | Before ingestion | Day 14 | Day 28 |
|---|---|---|---|
| Serum iron (µg/dL) | 92.9 ± 9.0 | 107.8 ± 9.7 | 119.6 ± 11.9 |

As is clear from Table 1, it can be seen that the serum iron concentration after ingestion (day 14 and day 28 from the start of ingestion) is significantly increased compared to before ingestion of the tablet (blood iron increasing agent, anemia improving agent) containing the lactic acid bacterium of the present invention.

Then, from this result, it can be seen that those containing lactic acid bacterium of the present invention (blood iron increasing agent, anemia improving agent) can satisfactorily increase the serum iron concentration. Therefore, it is found that it exerts an effect on the improvement of anemia (in particular, iron deficiency anemia) (it can be used as an anemia improving agent).

The above results were checked for significance. The significances were confirmed by Wilcoxon signed rank test. The risk rate (significance level) was 5%.

(Evaluation of Salt Tolerance of Lactic Acid Bacterium)

When the salinity of the medium was set at 12 w/v %, the proliferation rate was tested on the trade name "Lactic acid bacterium Kurahana LTK-1", on the lactic acid bacterium of Accession Number NITE BP-03010 (hereinafter, sometimes referred to as "ICK-3 Strain" or "ICK-3"), on "ICK-4 Strain" (sometimes referred to as "ICK-4"), and on "ICK-5 Strain" (sometimes referred to as "ICK-5"). Specific description will be made below.

(Medium)

As a nitrogen source and a trace mineral content, soy sauce (trade name "Koikuchi Soy Sauce" manufactured by Ichibiki Co., Ltd.) was used. As a carbon source, glucose (manufactured by Kanto Chemical Co., Inc.) was used. As other raw materials, salt (manufactured by Kanto Chemical Co., Inc.) and water were used. In this way, a medium consisting only of food raw materials was prepared.

Specifically, the above medium was prepared by mixing Koikuchi Soy Sauce, glucose, and salt with water so that Koikuchi Soy Sauce was 20 v/v %, glucose was 1.7 w/v %, and salinity was 12 w/v %, and then adjusting the pH to 7.0 with sodium hydroxide (Kanto Chemical Co., Inc.), a food additive.

The prepared medium was placed in a test tube (diameter: 18 mm×180 mm) in a volume of 10 mL, capped with SILICOSEN®, and sterilized in an autoclave at 121° C. for 15 minutes.

(Culture)

Lactic acid bacterium that had been pre-cultured in the above medium was added at a rate of 1 v/v %, assuming subculture. At this time, the number of bacteria at the time of initial culturing was $1.0 \times 10^7$ cfu/mL. This was cultured statically for 20 hours in an incubator at 30° C.

(Measurement of Number of Viable Cell)

After the static culture, the number of viable cells was measured. Determination of number of viable cells was performed by applying diluted bacterial solution to "10SG10N plating medium", followed by culturing (anaerobic culture at 30° C. for 4 days), and then counting the number of colonies.

The "10SG10N plating medium" containing 10 v/v % soy sauce (the trade name "Koikuchi Soy Sauce" manufactured by Ichibiki Co., Ltd.), 1.0 w/v % glucose, 1.0 w/v % yeast extract, 0.5 w/v % polypeptone, 0.2 w/v % sodium acetate 3 hydrate, 10 w/v % sodium chloride, 0.0025 w/v % "Tween80", 0.02 w/v % magnesium sulfate 7 hydrate, 0.001 w/v % manganese sulfate 4 hydrate, 0.001 w/v % iron sulfate 7 hydrate was pH6.8 and 2 w/v % agar.

The value obtained by dividing the number of bacteria after 20 hours of culturing by the number of bacteria at the time of initial culturing (the number of bacteria after 20 hours/the number of bacteria at the time of initial culturing) was calculated as the proliferation rate (times/20 hours) for 20 hours. Table 2 shows the results.

TABLE 2

|  |  | LTK-1 | ICK-3 | ICK-4 | ICK-5 |
|---|---|---|---|---|---|
| Initial | Number of Lactic acid bacterium Strains(cfu/mL) | 1.0E ± 07 | 8.20E ± 06 | 5.20E ± 06 | 6.80E ± 06 |
| After 20 hrs | Number of Lactic acid bacterium Strains(cfu/mL) | 3.5E ± 08 | 3.20E ± 08 | 5.90E ± 08 | 4.00E ± 08 |
|  | Proliferation Rate of Lactic acid bacterium (times/20 hrs) | 34 | 39 | 113 | 59 |

It can be seen that all of the lactic acid bacterium of the present invention proliferates vigorously even at a salinity of 12 w/v %. On the other hand, under such conditions of high salinity, it is usually difficult for other bacteria (contaminants such as unwanted bacteria) to proliferate. Therefore, by culturing lactic acid bacterium under conditions of high salinity, the lactic acid bacterium of the present invention is preferentially cultured even if contaminants are mixed, so that a culture can be easily obtained.

Example 2

Blood tests were performed on 9 healthy long-distance athletes from a company's team aged 22-27 years before (2 months, 4 months, 6 months) and after (2 months, 4 months)

ingestion of the lactic acid bacterium. The blood test was performed once every two months as described above.

Table 3 to Table 6 show the results of hemoglobin, serum iron, and ferritin in blood test items before and after ingestion of the lactic acid bacterium. In Tables 3 to 5, the "Mean value before the start of ingestion" indicates the mean value of each person of the blood tests performed 3 times before ingestion of the lactic acid bacterium (two months before, four months before, and six months before the start of ingestion). In addition, the "Mean value after the start of ingestion" indicates the mean value of each person of the blood tests performed twice after the ingestion of lactic acid bacterium (in the second month and the fourth month from the start of ingestion of the lactic acid bacterium).

In Table 6, the "Mean value before the start of ingestion" indicates the mean value of each person (A-I) of the blood tests performed 3 times before ingestion of the lactic acid bacterium (two months before, four months before, and six months before the start of ingestion). In Table 6, "2 months after the start of ingestion" indicates the results of each person (A-I) of the blood test performed two months after the start of ingestion of the lactic acid bacterium. "Four months after the start of ingestion" indicates the results of each person (A-I) on the blood test performed 4 months after the start of ingestion of the lactic acid bacterium.

As a method for ingesting the lactic acid bacterium, tablets (blood iron increasing agent, anemia improving agent) containing the lactic acid bacterium of the present invention (specifically, the lactic acid bacterium of Accession Number NITE BP-02318) and the trade name "Lactic acid bacterium Kurahana LTK-1" (manufactured by Ichibiki Co., Ltd.) were ingested orally together with water (2 tablets per day (containing 250 mg of "Lactic acid bacterium Kurahana LTK-1"). The ingestion period was 4 months as described above. The diet during the test was a normal diet that was not changed from usual diet.

Ingredients of orally ingested tablets are as follows: The trade name "Lactic acid bacterium Kurahana LTK-1" was 41.7% by mass, dextrin was 39.0% by mass, powdered cellulose was 15.0% by mass, sucrose fatty acid ester was 2.0% by mass, fine particulate silicon dioxide was 2.0% by mass, and shellac was 0.3% by mass.

The results of the blood tests are shown in Tables 3-6 below. Table 3 shows the change in serum iron concentration. Table 4 shows the change in ferritin concentration. Table 5 and Table 6 show the changes in hemoglobin concentration. "Serum iron concentration" is a value measured by a colorimetric method. "Ferritin concentration" is a value measured by CLIA (chemiluminescent immunoassay). "Hemoglobin concentration" is a value measured by SLS-hemoglobin method.

TABLE 3

|  | Mean value before the start of ingestion | Mean value after the start of ingestion |
|---|---|---|
| Serum iron (µg/dL) | 107 ± 30.1 | 122 ± 31.8 |

$P = 0.07$

As is apparent from Table 3, the serum iron concentration after ingestion of the tablet (blood iron increasing agent, anemia improving agent) containing the lactic acid bacterium of the present invention tends to increase as compared with before ingestion of the lactic acid bacterium of the present invention.

TABLE 4

|  | Mean value before the start of ingestion | Mean value after the start of ingestion |
|---|---|---|
| Ferritin (ng/ml) | 39.6 ± 20.6 | 54.2 ± 32.0 |

$P = 0.03$

As is apparent from Table 4, the concentration of ferritin after ingestion of the tablet (blood iron increasing agent, anemia improving agent) containing the lactic acid bacterium of the present invention is significantly increased as compared with before ingestion of the lactic acid bacterium of the present invention.

TABLE 5

|  | Mean value before the start of ingestion | Mean value after the start of ingestion |
|---|---|---|
| Hemoglobin (g/dL) | 14.2 ± 0.6 | 14.5 ± 0.7 |

$P = 0.06$

As is apparent from Table 5, the hemoglobin concentration after ingestion of the tablet (blood iron increasing agent, anemia improving agent) containing lactic acid bacterium of the present invention tends to increase as compared with before ingestion of the lactic acid bacterium of the present invention.

Table 6 shows the results of the blood tests performed on each tested person A to I, and it can be seen that the hemoglobin concentration tended to increase in 8 out of 9 tested persons in the blood test performed 4 months after the start of the ingestion of the lactic acid bacterium. In particular, it is considered that the tendency appears strongly in the tested person B, G, and I.

TABLE 6

|  | Mean value before the start of ingestion (g/dL) | 2 months after the start of ingestion (g/dL) | 4 months after the start of ingestion (g/dL) |
|---|---|---|---|
| A | 14.0 | 14.4 | 15.0 |
| B | 14.8 | 13.4 | 15.5 |
| C | 13.7 | 13.1 | 14.4 |
| D | 14.5 | 13.4 | 14.2 |
| E | 13.7 | 14.5 | 14.2 |
| F | 14.1 | 14.6 | 15.1 |
| G | 14.4 | 14.3 | 16.1 |
| H | 14.0 | 14.4 | 14.3 |
| I | 14.4 | 14.4 | 15.5 |

Example 3

The test in this example was conducted in a double-blind, parallel-group study. Fourteen Japanese women over 20 years old and under 59 years old who were judged to have "mild anemia" with a hemoglobin level of less than 12 g/dL and serum ferritin level of less than 12 ng/mL were included as the tested person (the test subject). These 14 patients were assigned to two groups (group A and group B). Thereafter, the test subjects in Group A (the test food ingestion group) were made to ingest orally two tablets of the test food (containing the lactic acid bacterium of the present invention) per a day together with water every day, and the test subjects in Group B (the control food ingestion group) were made to ingest orally two tablets of the tablet control food (containing no lactic acid bacterium of the present invention) per a day together with water every day. The ingestion period was 8 weeks.

Ingredient percentages of orally ingested tablets (test food and control foods) are as follows:

(Test Food)

The test food included a trade name "Lactic acid bacterium Kurahana LTK-1" (manufactured by Ichibiki Co., Ltd.) of 41.7% by mass, a dextrin of 39.0% by mass, a powdered cellulose of 15.0% by mass, a sucrose fatty acid ester of 2.0% by mass, a fine particle silicon dioxide of 2.0% by mass, and a shellac of 0.3% by mass. (Control food)

The control food included a dextrin of 79.7% by mass, powdered cellulose of 15.0% by mass, a sucrose fatty acid ester of 2.0% by mass, a fine particle silicon dioxide of 2.0% by mass, a caramel pigment of 1.0% by mass, and a shellac of 0.3% by mass.

In this example, the values of hemoglobin, serum iron, reticulocyte count, total iron binding capacity (TIBC), and serum ferritin, respectively, were measured before the start of ingestion and 8 weeks after the start of ingestion. The hemoglobin was measured by SLS-hemoglobin method, the reticulocyte count was measured by the flow cytometry method, the serum iron was measured by the colorimetric method, TIBC was measured by the colorimetric method, and the serum ferritin was measured by CLIA (chemiluminescent immunoassay). The results are shown in Table 7.

As can be seen in Table 7, in the control food ingestion group, there was no change in hemoglobin, but serum iron decreased, TIBC increased and serum ferritin decreased. This suggests that in the control food ingestion group, iron deficiency may be compensated for by storage iron to stop the decrease in hemoglobin.

On the other hand, in the test food ingestion group, both serum iron and serum ferritin increased suggesting that iron supply from food may exceed consumption. In addition, it has been reported that when iron deficiency anemia was treated with an iron preparation, the reticulocyte count increased in several days and the hemoglobin normalized in the subsequent six to eight weeks (See, Okada Sadamu: Treatment of Iron Deficiency Anemia, The Journal of the Japanese Society of International Medicine 99, 1220-1225 (2010)). Based on these reports, hemoglobin was not changed in the test food ingestion group as well as in the control food ingestion group in the results of the study period (8 weeks) in this example, but the reticulocyte count was increased in the test food ingestion group, suggesting that hemoglobin is an increasing situation. Therefore, in this example, the test period is 8 weeks, but if the test period is 8 weeks or longer, it is presumed that an increase in hemoglobin is confirmed.

Example 4

Three-week-old female mice (C57BL/6JJcl) were divided into eight groups containing 5 mice, and anemia model mice were prepared by being ingested low iron feed (powder) for 3 weeks to be anemic condition to all mice in all groups. During the following two weeks, the animals were fed each of the following feeds. Tables 9 to 12 show the blending prescription of the low iron feed (powder) and the normal feed. Table 9 shows the blending content of the feed (low iron feed (powder), normal feed), Table 10 shows the blending content of the respective mineral Mix of the low iron feed (powder) and the normal feed, and Table 11 shows the blending content of the vitamin Mix in the feed. In addition, Table 12 shows the content of iron in the feed (low iron feed (powder), normal feed).

The group fed the low iron feed containing 0.2% by mass of the lactic acid bacterium of Accession Number NITE BP-02318 (trade name "Lactic acid bacterium Kurahana LTK-1" (manufactured by Ichibiki Co., Ltd.)) was designated as the "LTK-1 feed group", the group fed the low iron feed containing 0.2% by mass of salt-tolerant lactic acid bacterium "ICK-3" was designated as the "ICK-3 feed group", the group fed the low iron feed containing 0.2% by mass of salt-tolerant lactic acid bacterium "ICK-4" was designated as the "ICK-4 feed group", and the group fed the low iron feed containing 0.2% by mass of salt-tolerant lactic acid bacterium "ICK-5" was designated as the "ICK-5 feed group". Three strains (No. 185 Strain (sometimes referred to as "No. 185"), No. 259 Strain (sometimes referred to as "No. 259") and No. 448 Strain (sometimes referred to as "No. 448") were also evaluated. The group fed the low-iron feed containing 0.2% by weight of salt-tolerant lactic acid bacterium "No. 185" was designated as the "No. 185 feed group", the group fed the low-iron feed containing 0.2% by weight of salt-tolerant lactic acid bacterium "No. 259" was designated as the "No. 259 feed group", and the group fed the low-iron feed containing 0.2% by weight of salt-tolerant lactic acid bacterium "No. 448" was designated as the "No. 448 feed group". Furthermore, the group fed the low iron feed containing no salt-tolerant lactic acid bacterium was designated as the "low iron feed group". All of the lactic acid bacterium used in this example belongs to *Tetragenococcus halophilus*.

In addition, during the test, the group in which normal food ("basic feed CE-2" manufactured by CLEA Japan, Inc.)

TABLE 7

| | | Control food ingested group (mean value) | | Test food ingested group (mean value) | |
|---|---|---|---|---|---|
| | | Before the start of ingestion | 8 weeks after the start of ingestion | Before the start of ingestion | 8 weeks after the start of ingestion |
| Blood test item | Hemoglobin (g/dL) | 10.80 ± 1.03 | 10.53 ± 0.91 | 10.8 ± 1.09 | 10.9 ± 1.47 |
| | Reticulocyte count (%) | 9.4 ± 2.9 | 9.7 ± 1.7 | 10.1 ± 2.3 | 11.9 ± 3.3 |
| | Serum iron (μg/dL) | 46.1 ± 20.2 | 41.9 ± 7.4 | 45.4 ± 20.9 | 49.3 ± 27.5 |
| | TIBC (μg/dL) | 431.0 ± 34.8 | 457.4 ± 44.2 | 440.0 ± 55.0 | 443.6 ± 54.9 |
| | Serum ferritin (ng/ml) | 6.79 ± 1.98 | 6.20 ± 1.81 | 5.29 ± 1.82 | 6.50 ± 2.87 |

In this example, the safety of ingestion of the trade name "Lactic acid bacterium Kurahana LTK-1" was also confirmed, and as a result, the adverse effect was not confirmed.

was ingested was designated as the "normal feed group". This normal feed group is mice that are not fed a low iron feed (powder) and are not anemic condition.

The breeding environment of the mice in each group was the same, specifically, as follows. Temperature was 20-26° C., humidity was 45-70% (excluding short-term changes during disinfection, etc.), and ventilation frequency was 10-15 times/hour. Illumination times ranged from 7:00 to 19:00 for bright hours and from 19:00 to 7:00 for dark hours. The microbiological grade was Specific pathogen free animals (SPF) (for aseptic breeding of experimental animals), the breeding racks were vinyl isolators (Max 8 cages), and the breeding cages were mouse PC (182×260×128 mm). Drinking water was filled into a water supply bottle (250 cc), and then water was supplied after high pressure steam sterilizing (121° C., 30 minutes). The timing of water supply was 1 bottle/2 times/week. The feeder used a special cover for cages, the bedding used shaving chips (high pressure steam sterilizing at 121° C. for 30 minutes) and the cage changed once a week.

Blood samples were collected at 3 weeks (i.e., at the time of feed switching) and 5 weeks (i.e., 2 weeks after feed switching) after the start of breeding, and blood hemoglobin concentrations were measured using a blood cell counter for animals (fully automatic blood cell counter) "Celltac α MEK-6458 (manufactured by Nihon Kohden). The results are shown in Table 8.

TABLE 8

|  | Week 3 (at feed switching) | Week 5 (2 weeks after feed switching) |
| --- | --- | --- |
| Normal feed group | 13.66 ± 0.34 | 13.14 ± 0.87 |
| LTK-1 feed group | 10.56 ± 1.33 | 11.86 ± 0.55 |
| ICK-3 feed group | 10.58 ± 0.92 | 11.58 ± 0.83 |
| ICK-4 feed group | 10.53 ± 0.86 | 12.15 ± 0.98 |
| ICK-5 feed group | 10.60 ± 0.88 | 12.02 ± 0.90 |
| No. 185 feed group | 10.62 ± 0.95 | 10.82 ± 1.05 |
| No. 259 feed group | 10.52 ± 0.87 | 11.32 ± 1.28 |
| No. 448 feed group | 10.58 ± 1.15 | 10.89 ± 1.35 |
| Low iron feed group | 10.54 ± 0.90 | 10.50 ± 0.46 |

** LTK-1 feed group, ICK-3 feed group, ICK-4 feed group, and ICK-5 feed group are significantly different from the low iron feed group in the risk rate of less than 5%.

As can be seen from Table 8, the blood hemoglobin concentration was increased in all groups that ingested the salt-tolerant lactic acid bacterium compared to the low iron feed group. Especially, in LTK-1 feed group, ICK-3 feed group, ICK-4 feed group and ICK-5 feed group, the blood hemoglobin concentration increased significantly compared with the low iron feed group. From these results, it was confirmed that ingesting feeds containing salt-tolerant lactic acid bacterium such as LTK-1, ICK-3, ICK-4, ICK-5, No. 185, No. 259, and No. 448 were effective in improving anemia. In particular, it is considered that lactic acid bacterium of LTK-1, ICK-3, ICK-4, ICK-5 are highly effective in improving anemia.

TABLE 9

| Content of feed (%) | |
| --- | --- |
| Cornstarch | 61.000 |
| Milk casein | 22.000 |
| Mineral Mix | 7.000 |
| Crystalline cellulose | 5.000 |
| Purified soybean oil | 4.000 |
| Vitamin Mix | 1.000 |
| Total | 100.000 |

TABLE 10

| Mineral Mix (mg/100 g feed) | Low iron feed (powder) (mg) | Normal feed (mg) |
| --- | --- | --- |
| $KH_2PO_4$ | 1,730.00 | 1,730.00 |
| $CaHPO_4 \cdot 2H_2O$ | 1,500.00 | 1,500.00 |
| $CaCO_3$ | 1,355.40 | 1,355.40 |
| $MgSO_4 \cdot 7H_2O$ | 800.00 | 800.00 |
| Cornstarch | 990.00 | 800.00 |
| NaCl | 600.00 | 600.00 |
| $FeC_6H_5O_7 \cdot nH_2O$ | — | 190.00 |
| $MnSO_4 \cdot 5H_2O$ | 15.40 | 15.40 |
| $2ZnCO_3 \cdot 3Zn(OH)_2 \cdot H_2O$ | 6.00 | 6.00 |
| $Ca(IO_3)_2$ | 1.54 | 1.54 |
| $CuSO_4 \cdot 5H_2O$ | 1.26 | 1.26 |
| $CoCl_2 \cdot 6H_2O$ | 0.40 | 0.40 |
| Total | 7,000.00 | 7,000.00 |

TABLE 11

| Vitamin Mix (mg/100 g feed) | |
| --- | --- |
| Cornstarch | 635.378 |
| Choline chloride | 300.000 |
| Vitamin E (50%) | 20.000 |
| Inositol | 15.000 |
| PABA | 10.150 |
| Nicotinic acid | 10.150 |
| D- Pantothenic acid Ca | 2.000 |
| Vitamin B2 | 1.872 |
| Vitamin B1 | 1.500 |
| Vitamin A (1 million IU/g) | 1.200 |
| Vitamin B6 | 1.020 |
| Biotin (2%) | 0.500 |
| Vitamin D3 (0.5 million IU/g). | 0.480 |
| Vitamin K3 | 0.300 |
| Vitamin B12 (2%) | 0.250 |
| Folic acid | 0.200 |
| Total | 1,000.000 |

TABLE 12

| | | Low iron feed (powder) | | Normal feed | |
| --- | --- | --- | --- | --- | --- |
| Raw material name | Content (%) | Blending ratio (%) | Content (%) | Blending ratio (%) | Content (%) |
| Milk casein | 0.0008 | 22.000000 | 0.00018 | 22.000000 | 0.00018 |
| Cornstarch | 0.0003 | 62.625378 | 0.00019 | 62.435378 | 0.00019 |
| $FeC_6H_5O_7 \cdot nH_2O$ | 16.6700 | — | — | 0.190000 | 0.03167 |
| Total (%) | — | — | 0.00036 | — | 0.03204 |

(Results and Discussion)

As shown in Table 1, it can be seen that the lactic acid bacterium of the present invention (the blood iron increasing agent of the present invention) has an effect of increasing the amount of iron in human serum by oral ingestion for a predetermined period of time. Further, from the results shown in Table 1, it can be seen that the lactic acid bacterium of the present invention (the blood iron increasing agent of the present invention) can be utilized as one capable of improving anemia (particularly, iron deficiency anemia).

From the results of Table 3 to Table 6, it can be seen that those containing the lactic acid bacterium of the present invention (blood iron increasing agent, anemia improving agent) can satisfactorily increase the serum iron concentration, the ferritin concentration, and the hemoglobin concentration. From this, it can be seen that it exerts an effect on the improvement of anemia (especially, iron deficiency anemia) (it can be used as an anemia improving agent).

Further, those containing the lactic acid bacterium of the present invention (blood iron increasing agent, anemia improving agent) exerts an effect on the improvement of sports anemia of athletes and people who are encouraging sports for health by increasing iron in blood (it can be used as an anemia improving agent). In addition to such an effect, an effect of improving the performance of the athlete (for example, an effect of improving the physical ability such as endurance) can be expected by enhancing aerobic exercise by promoting efficient oxygen transport in the body of the endurance athlete who is a player such as long-distance running.

Furthermore, from the results of Example 3 (Table 7), it was found that serum iron and serum ferritin were increased by ingesting the lactic acid bacterium of the present invention. Therefore, according to the lactic acid bacterium of the present invention, improvement of indefinite complaints due to latent anemia (latent iron deficiency) caused by lowering of serum ferritin can be expected.

In addition, from the results of Example 4 (Table 8), it can be seen that in addition to the lactic acid bacterium of Accession Number NITE BP-02318, it is also effective to increase the amount of iron in the serum by oral ingestion for a predetermined period of time for the lactic acid bacterium of Accession Number NITE BP-03010 (ICK-3 Strain), ICK-4 Strain, ICK-5 Strain, No. 185 Strain, No. 259 Strain, and No. 448 Strain. Although Example 4 is a mouse test, it can be inferred that the same effect is exhibited in humans.

INDUSTRIAL APPLICABILITY

The lactic acid bacterium of the present invention can be used as an active ingredient of a blood iron increasing agent or an anemia improving agent. The blood iron increasing agent of the present invention can be utilized as one for increasing the amount of iron in blood. The anemia improving agent of the present invention can be utilized as one for improving anemia (particularly, iron deficiency anemia).

Accession Number (1) Depositary Institution: NITE Patent Microorganisms Depositary, National Institute of Technology and Evaluation
Depositary Institution Address: Room 122, 2-5-8 Kazusakamatari, Kisarazu-shi, Chiba 292-0818, Japan
Date of deposit: Sep. 6, 2017
Accession number NITE BP-02318

(2) Depositary Institution: NITE Patent Microorganisms Depositary, National Institute of Technology and Evaluation
Depositary Institution Address: Room 122, 2-5-8 Kazusakamatari, Kisarazu-shi, Chiba 292-0818, Japan
Date of deposit: Aug. 5, 2019
Accession number NITE BP-03010

The invention claimed is:

1. A blood iron increasing composition comprising a salt-tolerant lactic acid bacterium, dextrin, cellulose, sucrose fatty acid ester, silicon dioxide, and shellac,
wherein the salt-tolerant lactic acid bacterium comprises a lactic acid bacterium of Accession number NITE BP-02318 or a lactic acid bacterium of Accession number NITE BP-03010, and
wherein the blood iron increasing composition contains about 10 billion to about 5 trillion in the number of salt-tolerant lactic acid bacteria.

2. The blood iron increasing composition according to claim 1, wherein the salt-tolerant lactic acid bacterium is isolated in a brewing process of miso.

3. The blood iron increasing composition according to claim 1, wherein a proliferation rate of the salt-tolerant lactic acid bacterium is 30 times/20 hrs or more when cultured in a medium having a salinity of 12 w/v %, wherein the proliferation rate is obtained by dividing the number of bacteria after 20 hours of culturing by the number of bacteria at the time of the initial culturing.

4. An anemia improving composition comprising a salt-tolerant lactic acid bacterium, dextrin, cellulose, sucrose fatty acid ester, silicon dioxide, and shellac,
wherein the salt-tolerant lactic acid bacterium comprises a lactic acid bacterium of Accession number NITE BP-02318 or a lactic acid bacterium of Accession number NITE BP-03010, and
wherein the anemia improving composition contains about 10 billion to about 5 trillion in the number of salt-tolerant lactic acid bacteria.

5. The blood iron increasing composition according to claim 2, wherein a proliferation rate of the salt-tolerant lactic acid bacterium is 30 times/20 hrs or more when cultured in a medium having a salinity of 12 w/v %, wherein the proliferation rate is obtained by dividing the number of bacteria after 20 hours of culturing by the number of bacteria at the time of the initial culturing.

6. The anemia improving composition according to claim 4, wherein the salt-tolerant lactic acid bacterium is isolated in a brewing process of miso.

7. The anemia improving composition according to claim 4, wherein a proliferation rate of the salt-tolerant lactic acid bacterium is 30 times/20 hrs or more when cultured in a medium having a salinity of 12 w/v %, wherein the proliferation rate is obtained by dividing the number of bacteria after 20 hours of culturing by the number of bacteria at the time of the initial culturing.

8. The anemia improving composition according to claim 6, wherein a proliferation rate of the salt-tolerant lactic acid bacterium is 30 times/20 hrs or more when cultured in a medium having a salinity of 12 w/v %, wherein the proliferation rate is obtained by dividing the number of bacteria after 20 hours of culturing by the number of bacteria at the time of the initial culturing.

9. The blood iron increasing composition according to claim 1, wherein the composition contains about 41.7% by mass of the salt-tolerant lactic acid bacterium, about 39.0% by mass of the dextrin, about 15.0% by mass of the cellulose, about 2.0% by mass of the sucrose fatty acid ester, about 2.0% by mass of the silicon dioxide, and about 0.3% by mass of the shellac.

10. The anemia improving composition according to claim 4, wherein the composition contains about 41.7% by mass of the salt-tolerant lactic acid bacterium, about 39.0% by mass of the dextrin, about 15.0% by mass of the cellulose, about 2.0% by mass of the sucrose fatty acid ester, about 2.0% by mass of the silicon dioxide, and about 0.3% by mass of the shellac.

* * * * *